(12) United States Patent
Hirschman

(10) Patent No.: US 7,439,234 B2
(45) Date of Patent: *Oct. 21, 2008

(54) METHOD FOR TREATING CANCER PATIENTS UNDERGOING CHEMOTHERAPY

(75) Inventor: Shalom Z. Hirschman, Riverdale, NY (US)

(73) Assignee: Advanced Viral Research Corporation, Yonkers, NY (US)

(*) Notice: Subject to any disclaimer, the term of this patent is extended or adjusted under 35 U.S.C. 154(b) by 731 days.

This patent is subject to a terminal disclaimer.

(21) Appl. No.: 10/456,668

(22) Filed: Jun. 5, 2003

(65) Prior Publication Data

US 2003/0206962 A1 Nov. 6, 2003

Related U.S. Application Data

(63) Continuation-in-part of application No. 08/839,651, filed on Apr. 15, 1997, now abandoned.

(51) Int. Cl.
*A01N 43/04* (2006.01)
*A01N 37/18* (2006.01)
*A61K 31/70* (2006.01)
*A61K 38/00* (2006.01)
*G01N 33/48* (2006.01)
*G01N 33/00* (2006.01)

(52) U.S. Cl. .............. 514/44; 514/2; 514/21; 514/44; 436/64; 436/86

(58) Field of Classification Search ............ 514/44, 514/2, 21, 814; 436/64, 86
See application file for complete search history.

(56) References Cited

OTHER PUBLICATIONS

Clinical Results of RETICULOSE in Patients with AIDS, 2 pages, Dec. 10, 1996.*
Chinnici, M.D., Angelo A. Communication by Plata Partners Limited Partnership, 7 pages, Jul. 6, 1992.*

* cited by examiner

*Primary Examiner*—Alana M. Harris
(74) *Attorney, Agent, or Firm*—Jenkins, Wilson, Taylor & Hunt, P.A.

(57) ABSTRACT

A method for treating cancer patients undergoing chemotherapeutic treatments by administering Product R, a peptide-nucleic acid preparation, is disclosed.

8 Claims, No Drawings

METHOD FOR TREATING CANCER PATIENTS UNDERGOING CHEMOTHERAPY

RELATED U.S. APPLICATION

This is a continuation-in-part application of U.S. patent application Ser. No. 08/839,651, filed Apr. 15, 1997, now abandoned. The contents of U.S. patent application Ser. No. 08/839,651 are hereby incorporated by reference in their entirety. The present application claims priority from U.S. application Ser. No. 08/839,651.

BACKGROUND OF THE INVENTION

I. Field of the Invention

The present invention relates to a method for using Product R as hereinafter defined to treat cancer patients undergoing chemotherapeutic treatments.

II. Description of the Related Art

Malignant, or cancerous, tumors are defined by their invasion of local tissue and their ability to spread or metastasize to other parts of the body. The incidence of such tumors is high; it is the second leading cause of death in both children and adults. A malignant tumor, by definition, always kills (unless treated) because of its invasive and metastatic characteristics. The tumor grows locally by encroachment into the normal tissues surrounding it. The tumor spreads to distant sites by the breaking off of malignant cells. These cells then move through the blood and lymphatic systems, attach themselves more or less remote site, and begin to grow as new colonies.

The factors controlling tumor growth are poorly understood. Tumors in laboratory animals may be transplanted to a second host using only a single tumor cell. This facility suggests that only one normal cell need become transformed (cancerous) for tumor growth to begin. It is thought, however, that many transformed cells die or remain latent or dormant for extended periods before successful tumor growth is established. Tumors have been experimentally induced in animals by chemical, physical, and viral agents, and by radiation and chronic irritation.

Immunological reactions can destroy neoplastic (potentially malignant) cells in vivo, and the accumulation of macrophages within a tumor can lead to its destruction. Cytotoxic T lymphocytes, natural killer (NK) cells, and activated macrophages can kill tumor cells in vitro. These observations suggest that the immune system provides some resistance against the development and spread of cancer, a contention strengthened by increased incidence of spontaneous tumors in individuals with congenital or acquired immune deficiency diseases.

Conventional treatment regimens for tumors include radiation and drugs or a combination of both. All of the conventional anti-cancer drugs are highly toxic and tend to make patients quite ill while undergoing treatment. Vigorous therapy is based on the premise that unless every cancerous cell is destroyed, the residual cells will multiply and cause a relapse.

Most of the conventional chemotherapeutic drugs that are being used in tumor therapy do not specifically kill tumor cells. Reliance is placed on the fact that, in most cancers, the cancerous cells grow faster than normal cells and will therefore utilize more of the toxic chemotherapeutic drug thereby specifically killing the cancer cell. Chemotherapy treatment is given either in a single or in several large doses or, more commonly, it is given in small doses 1 to 4 times a day over variable times from weeks to months. There is a large number of cytotoxic agents used to treat cancer and the mechanisms of the cytotoxic effects of each agent is frequently not known or only partially known. Administration of the conventional chemotherapeutic drugs requires careful attention to the amount and concentration of the drug or combination of drugs so that the cancer cells will be killed but normal cells will survive. For this reason, it is difficult to kill all cancerous cells by conventional chemotherapy. The successful use of chemotherapeutic agents to treat cancer depends upon the differential killing effect of the agent on cancer cells compared to effects on critical normal tissues.

The effects of chemotherapeutic agents on normal tissues are referred to as side-effects of cancer treatment. The immediate side effects (minutes to a few hours) of chemotherapy may include dizziness, nausea, vomiting, and diarrhea. These side effects are uncomfortable but, in themselves, are not life-threatening. Cell killing or damage within normal tissues that occurs from days to weeks after a commencement of a course of chemotherapy may result in uncomfortable and/or life threatening side effects. Among these effects are hair loss, hearing loss, sterility, damage to the mucosal epithelium of the gastrointestinal tract (namely, GI toxicity), damage to the oral mucosa, esophagus, small and large intestines, kidney damage, skin damage, cardiac damage, killing and suppression of the white blood cells which can lead to infection, reduction of platelets in the blood and killing of hematopoietic blood forming cells. Many of these side effects are related to tissues and organ systems that have a high number of dividing cells (proliferative cells). Some of these side effects are non-life threatening; however, a reduction or prevention of these effects could have a beneficial effect on cancer patients or make it possible to administer a higher dose of the chemotherapeutic agent while minimizing damage or death of cells in normal tissue.

Product R emerged as an antiviral product in the 1930's. The agent is known under the trademark RETICULOSE®, a trademark of Advanced Viral Research Corp. While it was originally believed to be a product composed of peptone, peptides and nucleic acids (fully defined hereafter), the precise composition remains unidentified. Nevertheless, Product R has demonstrated an ability to inhibit rapidly the course of several viral diseases. It is nontoxic, miscible with tissue fluids and blood sera and free from anaphylactogenic properties.

Insofar as the applicant knows, Product R has never been used, nor suggested for treating cancer patients having chemotherapeutic treatments. It is now discovered that Product R produces an unexpected result when employed to the patients having chemotherapeutic treatments.

SUMMARY OF THE INVENTION

An object of this invention therefore is to provide a method for treating cancer patients taking chemotherapeutic treatments through reducing side effects of chemotherapeutic agents on the cancer patients, or stimulating the immune system of the cancer patients, by administering parenterally to the patients Product R, an antiviral agent composed of peptides and nucleic acids.

Other objects and features of the present invention will become apparent from the following detailed description.

DETAILED DESCRIPTION OF THE PRESENTLY PREFERRED EMBODIMENTS

As used herein, Product R is a product manufactured by the Advanced Viral Research Corporation (Yonkers, N.Y.) and produced according to the following method.

METHOD FOR PREPARING PRODUCT R

Suspend about 35.0 g of casein, about 17.1 g of beef peptone, about 22.0 g of nucleic acid (RNA), about 3.25 g bovine serum albumin in about 2.5 liters of water for injection USP at about 3 to 7° C. in a suitable container and gently stir until all the ingredients have been properly wet. Carefully add while stirring about 16.5 g of sodium hydroxide (reagent grade ACS) and continue stirring until the sodium hydroxide is completely dissolved. Autoclave at about 9 lbs. pressure and 200-230° F. for a period of time until RNA is completely digested, for example, about 4 hours. At the end of the period, the autoclave is stopped and the reaction flask and contents are permitted to slowly cool to ambient temperature. Then cool for at least six hours at about 3-8° C. The resulting solution is filtered through 2 micron and 0.45 micron filters using inert gas such as nitrogen or argon at low pressure (1-6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165-210 mg/100 ml, the final volume is approximately 5 liters. The pH is then adjusted with either concentrated HCl (reagent grade ACS) or 1.0 normal NaOH to about 7.3-7.6 range. The diluted solution is then filtered again through 0.2 micron filters with inert gas at low pressure. The final filtrate is then filled and sealed into 2 ml glass ampules while in an inert gas atmosphere. The ampules are collected and autoclaved for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

The physical, chemical and biological properties of Product R are described in U.S. Pat. Nos. 6,303,153 and 6,528,098, the contents of which are incorporated by reference in their entirety.

For the patients having side effects of chemotherapeutic agents or suppressed immune system caused by chemotherapeutic agents, such as, for example, 6-mercaptopurine, adriamycin, bleomycin, cytoxan, chlorambucil, methotrexate, vincristine, 5-fluorouracil, cisplatinum, whether the chemotherapeutic agents are employed individually or in any combination, a suitable effective dose of Product R will be in the range of from about 5 microliters to about 40 microliters per kilogram of body weight per day, preferably in the range of about 10 microliters to about 25 microliters per kilogram of body weight per day. Most preferably Product R is administered in an amount of about 30 microliters per kilogram of body weight per day for about one week, followed by about 15 microliters per kilogram of body weight per day in a sterile injectable formulation. The desired dose may be administered as two, three or more sub-doses at appropriate intervals, generally equally spread in time, throughout the day. Preferably, the full daily dose is administered in one administration.

Product R may be administered by any suitable injection route including, but not limited to intravenously, intraperitoneally, subcutaneously, intramuscularly, and intradermally, etc. The presently preferred route of administration is intramuscularly. It will be appreciated that the preferred route may vary with, for example, the condition and age of the recipient.

Product R may be used in therapy in conjunction with other medicaments including corticosteroid, gamma globulin, glucose, or vitamins, antiviral agents such as interferon or interleukin, etc.

While it is possible for Product R to be administered as part of a pharmaceutical formulation, it is preferable to present it alone, although it may be administered at about the same time as one or more other pharmaceuticals are independently administered. If Product R is administered as part of a pharmaceutical formulation, the formulations of the present invention comprise at least one administered ingredient, i.e. Product R, as above defined, together with one or more acceptable carriers thereof and optionally other therapeutic ingredients. The carrier(s) must be "acceptable" in the sense of being compatible with the other ingredients of the formulation and not deleterious to the recipient thereof.

The formulations may conveniently be presented in unit-dose or multi-dose containers, e.g. sealed ampules and vials. Preferred unit dosage formulations are those containing a daily dose or unit, daily sub-dose, or an appropriate fraction of the administered ingredient.

Thus, while there have been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

EXAMPLE 1

Case 1 is that of a 36 year old white male with a history of widely metastatic and progressive malignant melanoma that involved brain, lung, liver, and spleen. He was begun on a regimen of temador (temazolarnide) 75 mg/m$^2$, and thalidomide 400 mg qhs. He tolerated the treatment with significant side effects—extreme fatigue and weight loss with loss of appetite because of gastric-intestinal (GI) toxicity caused by the chemotherapy. His performance status was KPS 60/100 when Product R 2 cc SC qd was added at his request. Within 24 hours of injection, he reported a substantial improvement in mood, appetite, and willingness to continue with his treatment. He maintained a normal CBC. This went on for approximately 2 weeks. Unfortunately, he then had a bleeding episode from a cerebral metastasis, and was noted to have progressed. He underwent palliative radiation and subsequently died of complications of pneumonia. He was not able to continue with Product R during his final hospitalization.

EXAMPLE 2

Case 2 is that of a 65 year old white male with a history of widely metastatic bladder cancer involving omentum and mesentery. He suffered from a severe neuropathy related to Taxol chemotherapy and progressed on it after an initial dramatic response. Gemzar was given with further progression and severe GI toxicity, manifested as loss of appetite, and extreme fatigue. Finally as a last attempt at palliation Taxotere with Product R therapy was given. The patient was able to improve his energy level, appetite, and was able to tolerate the Taxotere chemotherapy with no additional neurotoxicity, at essentially average dose (60 mg/m$^2$). He remained an actively treated patient and maintained his weight and heme parameters while on Product R, until he died at 2 months later of a stroke.

EXAMPLE 3

Case 3 is that of a 34 year old black female with advanced Hodgkin's disease who failed ABVD and stem cell transplant. She was not able to tolerate palliative Navelbine chemotherapy because of extreme fatigue and weight loss. She required doses of between 12-24 mg of dexamethasone to maintain any energy or appetite, and was transfusion dependent. In addition, cervical lymphadenopathy was causing severe pain and discomfort. Product R was added to the Navelbine regimen. Within 2 weeks the patient was maintaining weight, appetite, and although not complete, had an improvement in her ability to maintain a red cell count and platelet count. Because of extensive marrow involvement of the HD, she required intermittent use of growth factors. With the exception of one episode of blood borne sepsis due to an infected Mediport, the patient had been doing well with a significant decrease in overall lymphadenopathy and splenomegaly, based on a CT scan. She died 6 weeks later, when Product R was discontinued, of bacteremia.

EXAMPLE 4

Case 4 is that of a 72 year old male recently diagnosed with acute lymphocytic leukemia. His story is most dramatic. He arrived in New York on Jan. 10, 2001 after his oncologist in Florida stated that bone marrow done on January 7 showed relapse with 25% blasts. At that point, the dose of Product R which was started 3 weeks before was increased from 2 cc to 4 cc per day. He was profoundly fatigued and had lost 15 pounds. The WBC was 800 with 2000 blasts. Hemoglobin was 11.0, and platelet count was 110,000. Bactrim given as prophylactic therapy in Florida was discontinued and he was weaned off prednisone. He continued with Product R therapy, now approximately at 6 weeks of Product R treatment. He last received vincristine at the end of December 2000. He received 3 doses of G-CSF. By the next week his WBC improved and the G-CSF was discontinued. Two weeks later had a WBC of 10,000 with a normal differential. Hemoglobin was 14.2, hematocrit was 45, and platelet count was 157,000. A rare atypical lymphocyte was seen. A bone marrow aspirate and biopsy were done on Jan. 30, 2001 which revealed an occasional blast cell, as did the biopsy. Normal myeloid lines were seen with mild erythroid hyperplasia. The patent felt great, gained weight, and had improved strengths. He entered into a remission without additional cytotoxic therapy, only taking Product R.

I claim:

1. A method of maintaining and improving production of platelets in the blood in a cancer patient undergoing chemotherapeutic treatments, comprising administering parenterally to said patient an effective treatment amount of Product R in a sterile injectable formulation.

2. The method of claim 1 in which an effective treatment amount of Product R is in a range from about 5 microliters to about 40 microliters per kilogram of body weight per day in a sterile injectable formulation.

3. The method of claim 1 in which an effective treatment amount of Product R is in a range from about 10 microliters to about 25 microliters per kilogram of body weight per day in a sterile injectable formulation.

4. The method of claim 1 in which an effective treatment amount of Product R is about 30 microliters per kilogram of body weight per day in a sterile injectable formulation for about one week, followed by about 15 microliters per kilogram of body weight per day in a sterile injectable formulation.

5. A method of reducing gastric-intestinal toxicity in a cancer patient undergoing chemotherapeutic treatments, comprising administering parenterally to said patient an effective treatment amount of Product R in a sterile injectable formulation.

6. The method of claim 5 in which an effective treatment amount of Product R is in a range from about 5 microliters to about 40 microliters per kilogram of body weight per day in a sterile injectable formulation.

7. The method of claim 5 in which an effective treatment amount of Product R is in a range from about 10 microliters to about 25 microliters per kilogram of body weight per day in a sterile injectable formulation.

8. The method of claim 5 in which an effective treatment amount of Product R is about 30 microliters per kilogram of body weight per day in a sterile injectable formulation for about one week, followed by about 15 microliters per kilogram of body weight per day in a sterile injectable formulation.

\* \* \* \* \*